(12) United States Patent
Basir et al.

(10) Patent No.: US 7,183,930 B2
(45) Date of Patent: Feb. 27, 2007

(54) OCCUPANT HEARTBEAT DETECTION AND MONITORING SYSTEM

(75) Inventors: Otman Adam Basir, Waterloo (CA); Bosen Zhao, Guelph (CA)

(73) Assignee: Intelligent Mechatronic Systems Inc., Waterloo (CA)

( * ) Notice: Subject to any disclaimer, the term of this patent is extended or adjusted under 35 U.S.C. 154(b) by 72 days.

(21) Appl. No.: 10/894,422

(22) Filed: Jul. 19, 2004

(65) Prior Publication Data

US 2005/0027416 A1 Feb. 3, 2005

Related U.S. Application Data

(60) Provisional application No. 60/488,863, filed on Jul. 18, 2003.

(51) Int. Cl.
*G08B 23/00* (2006.01)
*G08B 19/00* (2006.01)
*A61B 5/02* (2006.01)

(52) U.S. Cl. .................. 340/573.1; 340/521; 340/522; 600/301; 600/509; 600/527

(58) Field of Classification Search ............. 340/573.1; 600/527
See application file for complete search history.

(56) References Cited

U.S. PATENT DOCUMENTS

| 4,320,766 | A | 3/1982 | Alihanka et al. |
| 4,706,072 | A | 11/1987 | Ikeyama |
| 5,448,996 | A | 9/1995 | Bellin et al. |
| 5,574,641 | A | 11/1996 | Kawakami et al. |
| 5,738,102 | A | 4/1998 | Lemelson |
| 5,853,005 | A | 12/1998 | Scanlon |
| 5,882,300 | A | 3/1999 | Malinouskas et al. |
| 5,964,720 | A | 10/1999 | Pelz |
| 6,067,019 | A | 5/2000 | Scott |
| 6,485,441 | B2 | 11/2002 | Woodward |
| 6,498,652 | B1 | 12/2002 | Varshneya et al. |
| 6,547,728 | B1 | 4/2003 | Cornuejols |
| 6,547,743 | B2 | 4/2003 | Brydon |
| 2003/0233034 | A1 | 12/2003 | Ruotsalainen |

FOREIGN PATENT DOCUMENTS

| WO | WO 00/20258 | 4/2000 |
| WO | WO 01/02823 | 1/2001 |

OTHER PUBLICATIONS

International Search Report, Nov. 22, 2004.

*Primary Examiner*—Donnie L. Crosland
(74) *Attorney, Agent, or Firm*—Carlson, Gaskey & Olds

(57) ABSTRACT

The disclosed invention uses two sensors to capture the heartbeat and environmental noises of an occupant of a vehicle or hospital bed. One of the sensors is placed on a seat or bed frame adjacent the occupant. A second sensor is placed remotely from the occupant, on a vehicle floor, or remote portion of the bed frame. A signal conditioning module is attached to the first and second sensors for detecting the heartbeat signal. Specialized software is used for processing the signal and decision making based upon the extracted heartbeat signal. The invention is capable of operating despite environmental noise and vibrations.

30 Claims, 3 Drawing Sheets

OCCUPANT HEARTBEAT DETECTION AND MONITORING SYSTEM

This application claims priority to U.S. Provisional Application Ser. No. 60/488,863, filed Jul. 18, 2003.

BACKGROUND OF THE INVENTION

The present invention relates to a heartbeat sensing system. More specifically to a heartbeat sensing system which is incorporated into a vehicle seat or hospital bed to monitor an occupant.

Heartbeat sensing systems are commonly used to monitor occupants of vehicles, beds, etc. The sensing systems can be used to detect the presence of an occupant. Often alarms are attached to the sensing systems to cause an alert in cases of heartbeat cessation, unusual heart rate activity, or occupant drowsiness.

Heartbeat sensing systems in vehicles are typically placed in an area that will be adjacent an occupant, for example, in a seat belt or seat. Vibration sensors are typically used to detect a heartbeat. In order for the heartbeat sensing system to be useful it must be able to detect the heartbeat separately from the environmental noise, such as the engine and/or road vibrations.

Heartbeat sensing systems in hospital beds may be attached to sheets or strips that are placed between the bed and the patient. While this type of monitoring system eliminates the need for wires directly on an occupant's body the monitoring system is susceptible to patient's movements. In addition, monitoring heartbeat during transportation of the patient can be difficult due to vibrations resulting from the transport vehicle that are picked up by the sensors obscuring the heartbeat.

Thus a heartbeat sensing system is needed that is unobtrusive to an occupant and which can filter out environmental noise is needed.

SUMMARY OF THE INVENTION

The disclosed invention uses two vibration or acceleration sensors to capture the heartbeat and environmental noises of an occupant of a vehicle seat or hospital bed.

One of the sensors is placed on a seat or bed frame adjacent the occupant. The first sensor will detect the heartbeat of an occupant, but the signal from the first sensor will also include environmental noise. The environmental noise could be vibrations from a running engine, vibrations from feedback from the road, vibrations created by movements of a patient, or movements of the bed, or the like. A second sensor is placed remotely from the occupant, on a vehicle floor, or remote portion of the bed frame. The signal from the second sensor will include the environmental noise, but will not significantly include the occupant heartbeat because it is placed in a location that will not significantly receive the heartbeat signal.

A signal conditioning module is attached to the first and second sensors for detecting and monitoring the heartbeat signal. The signal conditioning module includes a multi-level amplifier, a low pass filter, and a signal processing unit. Specialized software is used for processing the signal and decision making based upon the extracted heartbeat signal. The invention is capable of operating despite environmental noise and vibrations.

These and other features of the present invention will be best understood from the following specification and drawings, the following of which is a brief description.

DETAILED DESCRIPTION OF THE PREFERRED EMBODIMENT

Figure 1:
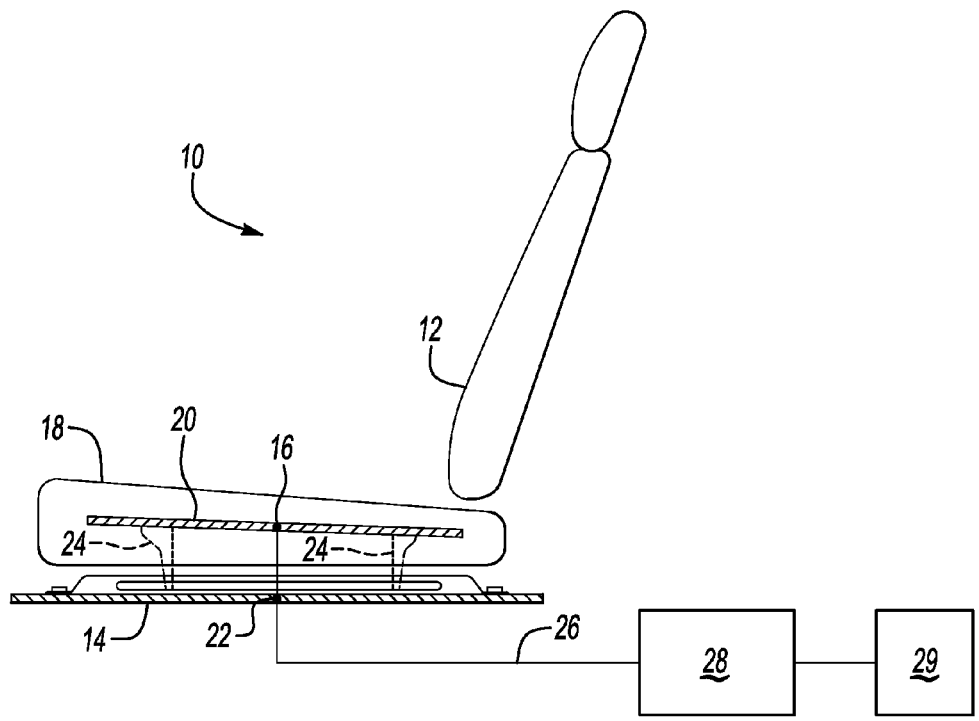
FIG. 1 is a side view of a first embodiment of the present invention showing a vehicle seat with the heartbeat sensing system.

FIG. 1 illustrates a general view of a heartbeat sensing system 10 in a vehicle. A vehicle seat 12 is mounted on a vehicle floor 14. A first sensor 16 is placed in the vehicle seat 12. The first sensor 16 is preferably placed in a lower seat portion 18 on the seat frame 20. A second sensor 22 is placed on the vehicle floor 14. Seat support structure 24 supports the lower seat portion 18 on the vehicle floor 14. Wiring 26 connects the first sensor 16 and second sensor 22 to a signal conditioning module 28. The signal conditioning module 28 determines the heartbeat of the occupant in a manner described below and sends the heart rate to a response system 29, which uses the heart rate as an input for determining a response.

Figure 2:
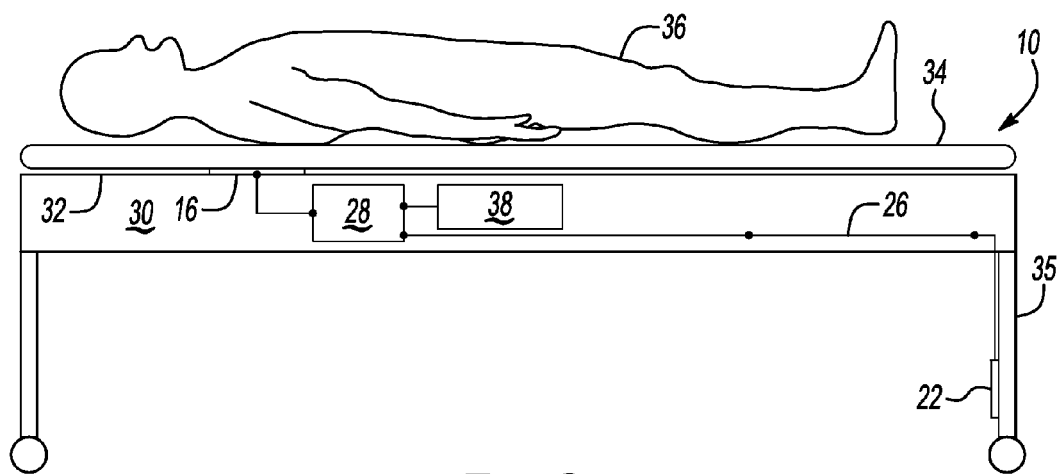
FIG. 2 is a side view of a second embodiment of the present invention showing a hospital bed with the heartbeat sensing system.

FIG. 2 illustrates a general view the heartbeat sensing system 10 installed in a hospital bed 30. The first sensor 16 is attached to a bed frame 32 near the likely position of the occupant's heart. The bed 30 may be a hospital bed, gurney, operating table, stretcher, or the like. A mattress or sheet 34 may be placed on the bed 30 between the occupant 36 and the first sensor 16. The second sensor 22 may be mounted on the bed 30 in a position remote from the occupant's heartbeat. Both the first sensor 16 and second sensor 22 are connected to the signal conditioning module 28, by means of wiring 26. Bed support structure 35, such as the frame and legs, separate the first sensor 16 and the second sensor 22. The signal conditioning module 28 may be connected to a monitor 38 for monitoring the heartbeat. The signal conditioning module 28 and the monitor 38 may be mounted on the bed 30 such that wiring between the first sensor 16, the second sensor 22, the signal conditioning module 28, and the monitor 38 is removed from sight.

In both the first and second embodiment the first sensor 16 receives vibrations from the heartbeat. However, vibrations from the environment may be received as well obscuring the heartbeat signal. The second sensor 22 is remote from the location of the occupant 36. The second sensor 22 is preferably separated from the first sensor 16 by the support structure of the vehicle seat 12 or bed 30. Because the second sensor 22 is remote from the occupant most of the vibrations received by the second sensor 22 will be from movement resulting from a vehicle running, or the rolling of the bed 30, etc.

Figure 3:
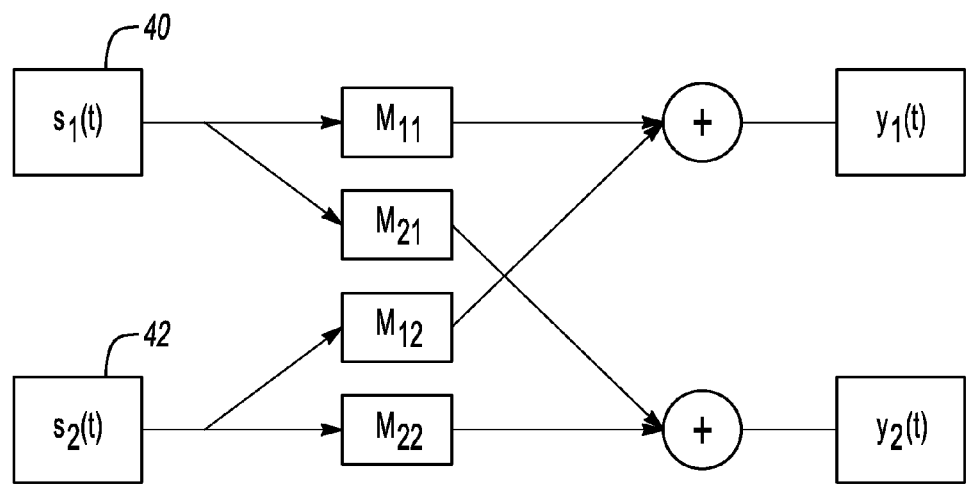
FIG. 3 is a schematic showing the vibration signal mixing.

FIG. 3 shows a schematic of signal mixing that occurs. $S_1(t)$ represents the signal dominantly from the heart and $S_2(t)$ the signal from the vehicle floor 14 or the bed frame 32. $M_{11}$, $M_{12}$, $M_{21}$ and $M_{22}$ are transfer functions from a first source 40 (the heart) to the first sensor 16, first source 40 to the second sensor 22, a second source 42 (the vehicle floor 14 or the bed frame 32) to the first sensor 16 and the second source 42 to the second sensor 22. Using a digital signal adaptive filtering technique and the signals of the second sensor 22 as a reference, the environmental vibration signal can be suppressed from the vibration signal of first sensor 16.

Figure 4:
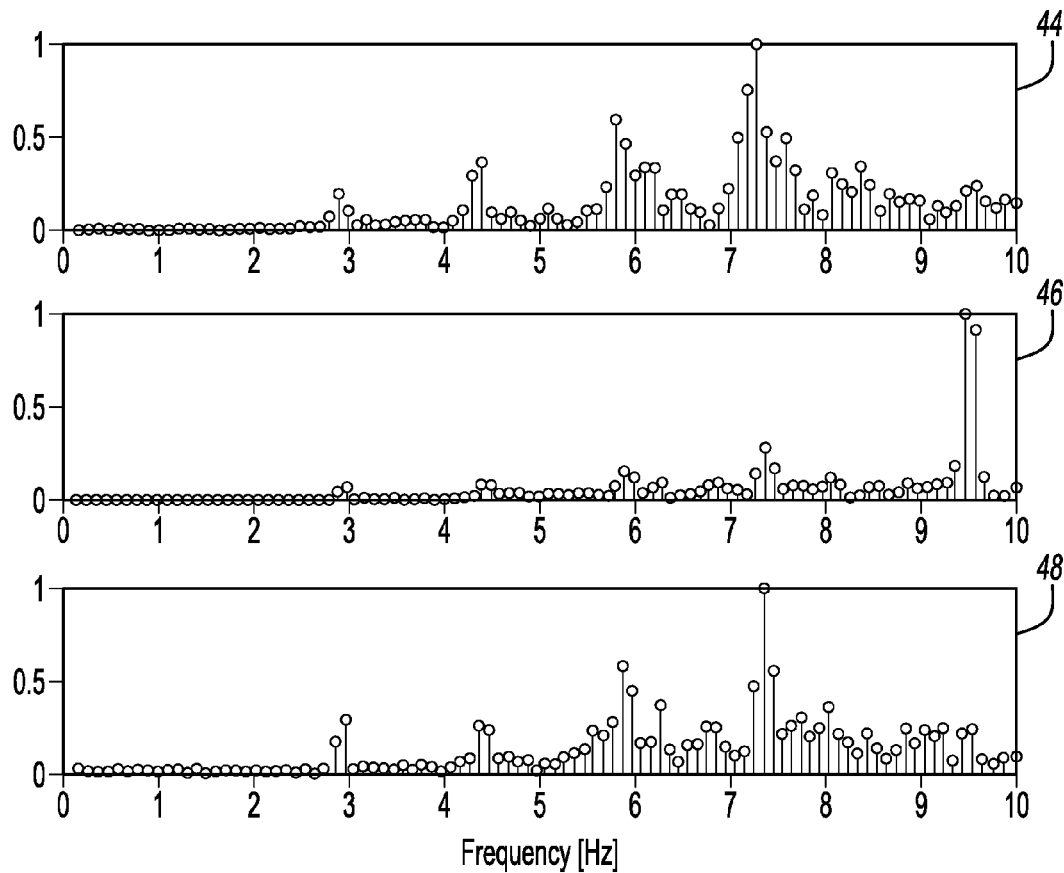
FIG. 4 is a heart beat spectrum showing before and after the environmental noise has been filtered.

FIG. 4 is an example using adaptive filtering technique to extract the real heart beat signal, in which the first spectrum 44 is sampled by the first sensor 16 with an occupant 36 lying on a stationary bed 30, or sitting in a non-running vehicle. The second spectrum 46 represents the signal from the first sensor 16 with occupant 36 lying on a moving bed 30, or sitting in a running or moving vehicle. The third spectrum 48 is the result using adaptive filtering of reference signals sampled simultaneously by the first sensor 16 and the second sensor 22. It can be seen the heart beat spectrum is recovered by this technique.

Figure 5:
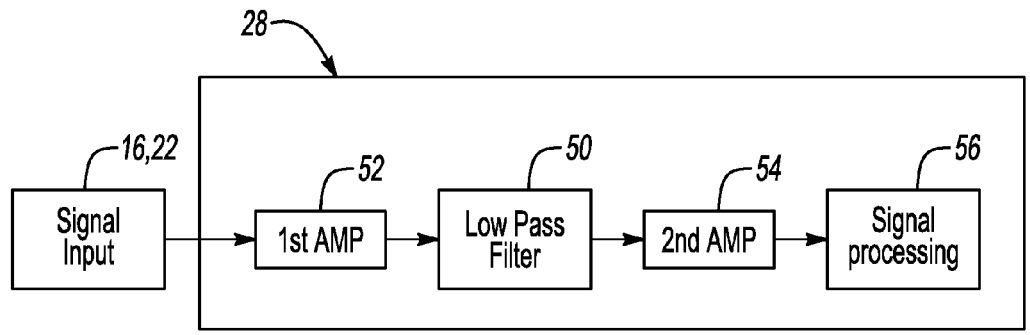
FIG. 5 is an embodiment of a signal conditioning module.

Some special concerns are paid to a signal conditioning module as shown in FIG. 5. This is because the analog signal, sampled by the first sensor 16 and the second sensor 22, needs to go through a low-pass filter 50 before digitization for further adaptive filtering. However, a conventional physical filter cannot work correctly since the heartbeat signal is extremely small. Consequently, signal amplification is needed before filtering. On the other hand, gain cannot be set too high since the first sensor 16 is also subject to high levels of background vibration signals. The gain is designed such that the heartbeat signal is amplified at the point of first amplifier 52 just above the low threshold to allow for the working functionality of the low-pass filter. Signals pass to the low-pass filter with a cut-off frequency of 10 Hz, for example, after the first level amplification. Then the after-filtering signal is amplified by the second level amplifier 54 to the amplitude suitable for an A/D converter operation, performed by the signal processing unit 56. An overload protection circuit is also integrated in the conditioning circuit.

Figure 6:
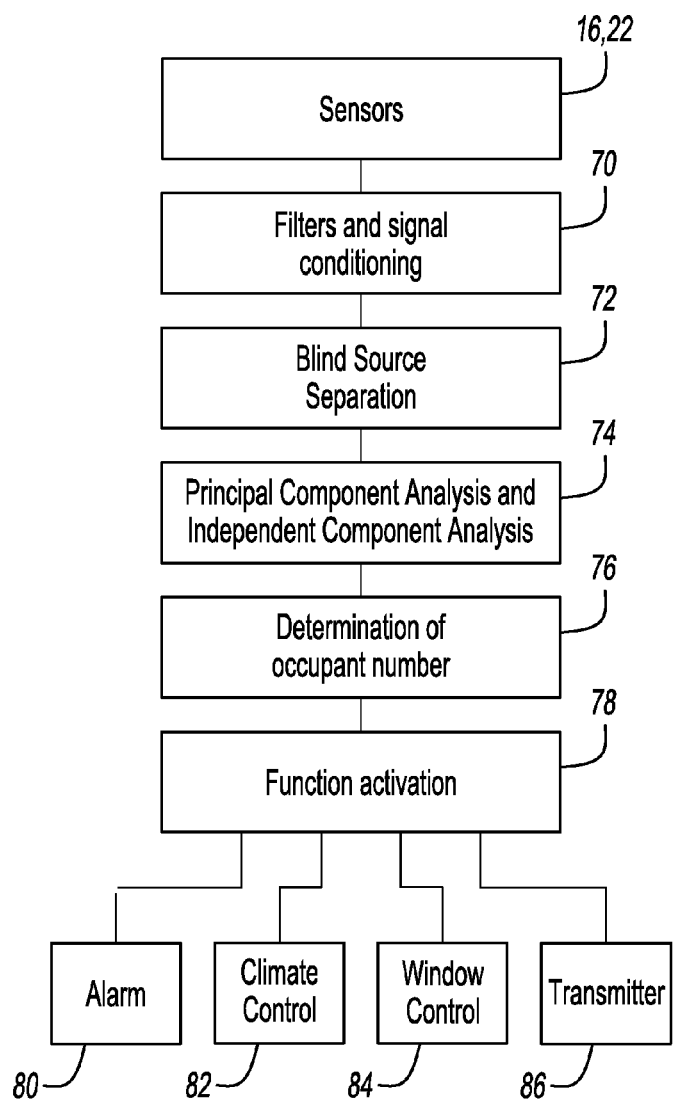
FIG. 6 is a flow chart of the operation of the heartbeat detection system.

The last portion of the signal conditioning module 56 is the signal processing unit 56 which completes the adaptive signal filtering based upon the transfer functions of FIG. 3. FIG. 6 is a flowchart of the heartbeat detection system. Vibration signals from the seat 12 and floor 14 (or bed 30) are sampled through the sensors 16, 22. Signal conditioning is performed as described above in step 70. Blind source separation 72 and Principal Component Analysis and Independent Component Analysis 74 are then performed based upon the transfer functions (FIG. 3). In step 76, it is determined whether an occupant is present in the vehicle seat 12 (or bed 30) and the total number of occupants in the vehicle seats 12 (in the case of a vehicle seat 12). In step 78, function activation occurs based upon the existence and/or the level of the occupant's heartbeat, such as activating an alarm 80, climate control 82, window control 84 and/or activating a transmitter 86 (such as calling for emergency assistance).

In vehicle seat 12 example of FIG. 1, for example, the function activation step 78 is the activation of the response system 29, which may be an occupant presence detection system and/or a drowsiness detection system that alters the climate control system and/or generates an alarm based upon a determination that the alertness of the occupant has dropped below a predetermined threshold. One suitable drowsiness detection system is disclosed in U.S. application Ser. No. 10/348,037, filed Jan. 21, 2003, now U.S. Pat. No. 6,822,573, which is hereby incorporated by reference in its entirety.

The heartbeat detection system 10 may also be used to prevent solar heat or lack of oxygen accidents to children, disabled adult passengers or pets who may become trapped or are left waiting in a vehicle under extreme temperature conditions. The occupant heartbeat detection system 10 can be used to lower the windows in step 84, trigger an alarm in step 80 or activate the appropriate the climate control system in step 82. The occupant heartbeat detection system 10 may also be used during normal driving conditions to optimize climate control in the vehicle to provide the occupants with the desired comfort. In the case of a crash, the heartbeat data can be transmitted in step 86 to emergency service providers to provide them with information about the health conditions of the occupants.

Although a preferred embodiment of this invention has been disclosed, a worker of ordinary skill in this art would recognize that certain modifications would come within the scope of this invention. For that reason, the following claims should be studied to determine the true scope and content of this invention.

We claim:

1. A heartbeat sensing system comprising:
   an occupant support having an occupant support surface;
   a first sensor proximate said occupant support surface and generating a first sensor signal;
   a second sensor remote from said occupant support surface and generating a second sensor signal; and
   a signal conditioning module connected to said first sensor and said second sensor for processing the first sensor signal and the second sensor signal to detect a heartbeat, wherein the second sensor is proximate a floor on which said occupant support is supported.

2. The system of claim 1 further including a support structure between said occupant support and said second sensor.

3. The system of claim 1, wherein the second sensor is proximate a floor on which said occupant support is supported.

4. The system of claim 1, wherein said signal conditioning module is operably connected to a response system to trigger a response based upon said heartbeat.

5. The system of claim 1, wherein said signal conditioning module includes a multi-level amplifier, a low pass filter, and a signal processing unit.

6. The system of claim 5, wherein said signal processing unit includes decision making software for communicating with a response system.

7. The system of claim 1 wherein the signal conditioning module uses the second sensor signal in adaptive filtering to remove noise from the first sensor signal.

8. A heartbeat sensing system comprising:
   a first sensor mounted to a vehicle seat;
   a second sensor mounted proximate a vehicle floor; and
   a signal conditioning module connected to said first sensor and said second sensor for processing a first sensor signal from said first sensor and a second sensor signal from said second sensor to detect a heartbeat.

9. The heartbeat sensing system of claim 8, wherein said signal conditioning module includes a multi-level amplifier, a low pass filter, and a signal processing unit.

10. The heartbeat sensing system of claim 9, wherein said multi-level amplifier is a two-stage amplifier located before and after said low pass filter for amplifying said first signal and said second signal.

11. The heartbeat sensing system of claim 8, wherein said signal conditioning module is operably connected to a vehicle system to trigger a response based upon said heartbeat.

12. The heartbeat sensing system of claim 11, wherein said vehicle system is an occupant detection system.

13. The heartbeat sensing system of claim 11, wherein said vehicle system is a driver alertness alarm.

14. The heartbeat sensing system of claim 11, wherein said vehicle system is a climate control system.

15. The system of claim 8 wherein the signal conditioning module uses the second sensor signal in adaptive filtering to remove noise from the first sensor signal.

16. A heartbeat sensing system comprising:
   a first sensor mounted to a bed frame adjacent an occupant area;
   a second sensor mounted to a bed frame remote from said first sensor; and
   a signal conditioning module connected to said first sensor and said second sensor for processing a first sensor signal from said first sensor and a second sensor signal from said second sensor to detect a heartbeat.

17. The heartbeat sensing system of claim 16, wherein said signal conditioning module includes a multi-level amplifier, a low pass filter, and a signal processing unit.

18. The heartbeat sensing system of claim 17, wherein said multi-level amplifier is a two-stage amplifier located before and after said low pass filter for amplifying said first signal and said second signals.

19. The heartbeat sensing system of claim 16, wherein said signal conditioning module is operably connected to a system to trigger a response based upon said heartbeat.

20. The heartbeat sensing system of claim 19, wherein said system is an occupant detection system.

21. The heartbeat sensing system of claim 19 wherein said system is a heart condition alarm.

22. The system of claim 16 wherein the signal conditioning module uses the second sensor signal in adaptive filtering to remove noise from the first sensor signal.

23. A method of monitoring a heartbeat comprising the steps of:
   a) monitoring vibration at a first location proximate an occupant heart;
   b) monitoring vibration at a second location remote from the occupant heart and the first location; and
   c) using the vibration at the second location to remove noise from the vibration at the first location to determine an occupant heartbeat.

24. The method of claim 23, wherein said step c) further includes filtering environmental noise from said first sensor signal to detect said heartbeat.

25. The method of claim 24, wherein said step c) further includes comparing the first sensor signal and the second sensor signal to distinguish a heartbeat signal from the environmental noise.

26. The method of claim 24, wherein said step c) includes using principal component analysis to distinguish a heartbeat signal from the environmental noise.

27. The method of claim 24, wherein said step c) includes using independent component analysis to distinguish a heartbeat signal from the environmental noise.

28. The method of claim 23, further comprising:
   d) triggering a response in a system connected to the signal conditioning module.

29. The method of claim 23, wherein said step c) further includes amplifying the first and second sensor signals using a multi-level amplifier.

30. The method of claim 23, wherein said step c) further includes passing the first and second sensor signals through a low pass filter.

* * * * *